United States Patent [19]

D'Amico

[11] Patent Number: 4,941,869
[45] Date of Patent: Jul. 17, 1990

[54] OSTOMY PLUG-POUCH

[76] Inventor: Ben A. D'Amico, 563 Emily Dr., Lilburn, Ga. 30093

[21] Appl. No.: 258,872

[22] Filed: Oct. 17, 1988

[51] Int. Cl.$^5$ .............................................. A61F 5/44
[52] U.S. Cl. ...................................... 600/32; 604/337; 604/277
[58] Field of Search ................ 604/328, 277, 332–345; 600/29–32

[56] References Cited

U.S. PATENT DOCUMENTS

| | | | |
|---|---|---|---|
| 3,089,493 | 5/1963 | Galindo | 604/344 |
| 4,318,406 | 3/1982 | McLeod | 604/333 |
| 4,419,100 | 12/1983 | Alexander | 604/339 |
| 4,465,486 | 8/1984 | Hill | 604/338 |
| 4,596,566 | 6/1986 | Kay | 604/343 |
| 4,721,508 | 1/1988 | Burton | 604/277 |
| 4,723,952 | 2/1988 | Esposito | 604/338 |

Primary Examiner—Jerome L. Kruter
Attorney, Agent, or Firm—Harry I. Leon

[57] ABSTRACT

An ostomy pouch having a plug for the stoma and a pouch to collect natural discharges. The plug stops the natural discharges from collecting in the pouch. The pouch is employed to catch any discharges that might leak through the plug and to form a reservoir when the plug is dislodged. Such a reservoir is especially required when one is in training for the use of the stoma plug. The pouch has an openable top through which the user can reach to remove the stoma plug so that the contents of the colon can be drained into the pouch. The bottom of the pouch is also openable, allowing the user, when sitting on a water closet, to drain the pouch into the toilet without undressing any more than would a person without a colostomy. After discharge of the pouch, the bottom drain can be resealed, the plug placed back into the stoma, and the top of the pouch closed.

The pouch is detachably mounted on a person's body. As confidence and control in the use of the ostomy plug is developed, the pouch can be used less and less.

6 Claims, 3 Drawing Sheets

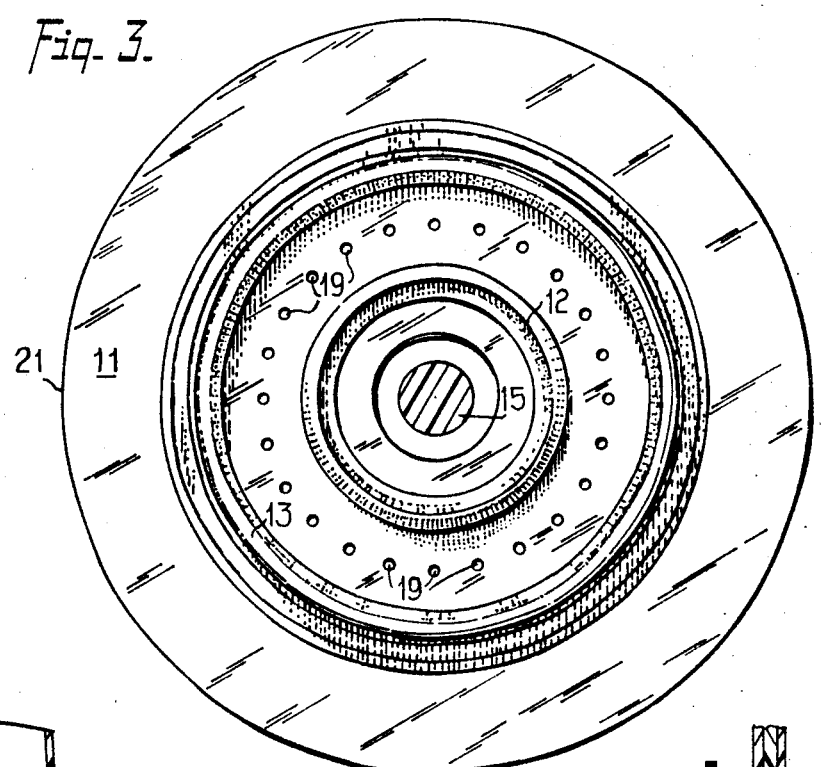
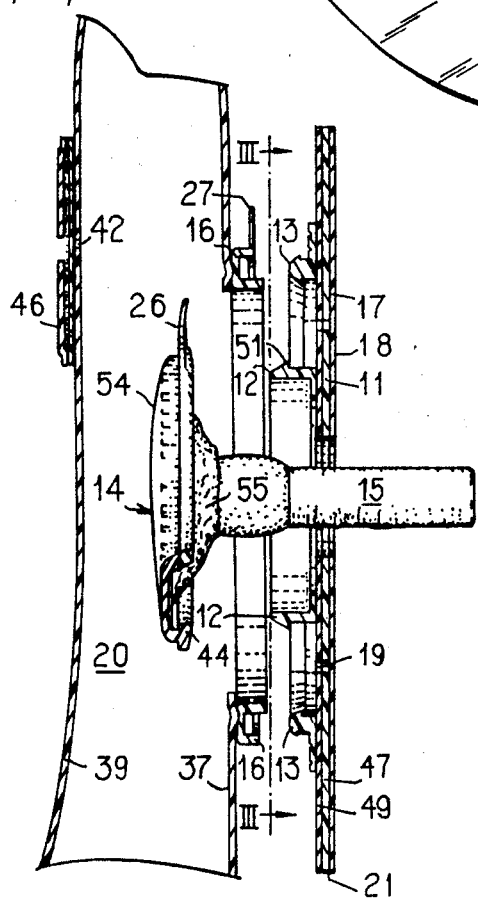
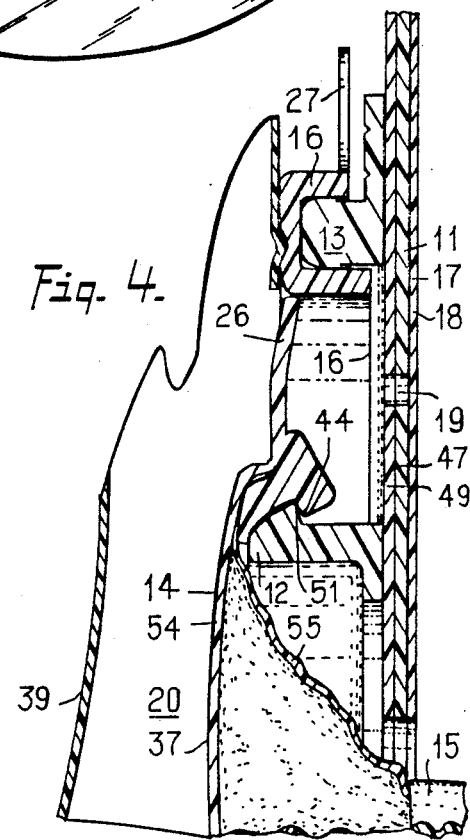

OSTOMY PLUG-POUCH

BACKGROUND OF THE INVENTION

This invention relates to medical and patient care apparatus for colostomy patients. The use of a plug in the stoma allows colostomy patients freedom from having to wear a pouch attached to their person to collect natural discharges.

McDonnell, U.S. Pat. No. 4,121,589, discloses a plug that is insertable into the stoma. The plug, which is held in place by a flange with an adhesive surface on the side thereof facing the patient, protrudes only slightly from the wearer's body. McDonnell's device closely parallels one known as the Conseal Plug marketed by Coloplast, Inc. The Conseal plug when under pressure from fluids inside the intestine has been found, however, to leak through the adhesive mounting of the flange. This leakage is especialy common in the case of persons just learning to use such a plug. The embarrassment to the patient from the leakage detracts from his trying the plug long enough to become accustomed to its use.

SUMMARY OF THE INVENTION

The invention is an unique combination of a stoma plug and a colostomy pouch which answers the needs of a colostomy patient who wants not only freedom from the restraint and embarrassment of having to wear a bulging, partially filled colostomy pouch but also from the leakage that may occur when only a stoma plug is worn.

The ostomy plug-pouch according to the present invention includes a support pad with a flexible protective layer having an opening through which a patient's stoma can be fitted. The protective layer is secured to the person's body by adhesive or glue. This protective layer underlies a thin, thermoplastic material from which protrudes a pair of generally concentric mounting rings. Mating rings on the plug and on the pouch form seals with the mounting rings and allow the plug and the pouch to be detachably coupled to the base.

In the present invention, the pouch is mounted around the stoma plug in such a way that if any leakage occurs, the leakage is contained within the pouch. To help direct all of the fluid exiting the stoma into the pouch, relief ports are incorporated into the support pad so that fluid which may seep beneath it is also collected in the pouch. Thus the leakage can be totally contained, thereby eliminating a potential source of embarrassment to the patient.

The detachable coupling between the pouch and the support pad allows one to use the plug alone or with the pouch. When added protection is required, the use of both the plug and pouch is recommended. Such protection is especially needed when one is first becoming accustomed to using the plug. When the pouch is used with the plug, the ostomy plug-pouch remains flat and virtually undetectable under clothing. If the patient feels a need to relieve intestinal pressure, he can dislodge the ostomy plug by grabbing a hold on its release handle even through his clothing and allow the natural discharge to drain into the pouch. Once the discharge enters the pouch, it functions much as does a standard ostomy pouch which is drainable at the patient's convenience. The lower end of the pouch is both openable and resealable, allowing the contents thereof to be drained into a toilet without the wearer's detaching the pouch. The top of the pouch is also openable and resealable. After the pouch is drained, the patient can open the top and either replace the used plug or insert a new plug in the stoma.

The pouch is also equipped with means for venting and de-odorizing natural gas discharges. As a result, the ostomy plug-pouch not only allows the patient a flexible means for maintaining an active life but is in some ways superior to the natural method of body waste control.

BRIEF DESCRIPTION OF THE DRAWINGS

The present invention may be more readily described by reference to the accompanying drawing in which:

FIG. 2 is an exploded view from the side partially in cross section of a fragmentary portion on an enlarged scale of the ostomy-plug pouch according to FIG. 1;

FIG. 3 is a cross-section III—III from FIG. 2;

FIG. 4 is a greatly enlarged fragmentary sectional view showing both the plug and the pouch coupled to the support pad in the ostomy-plug pouch according to FIG. 1;

DETAILED DESCRIPTION OF THE PREFERRED EMBODIMENT

Figure 1:
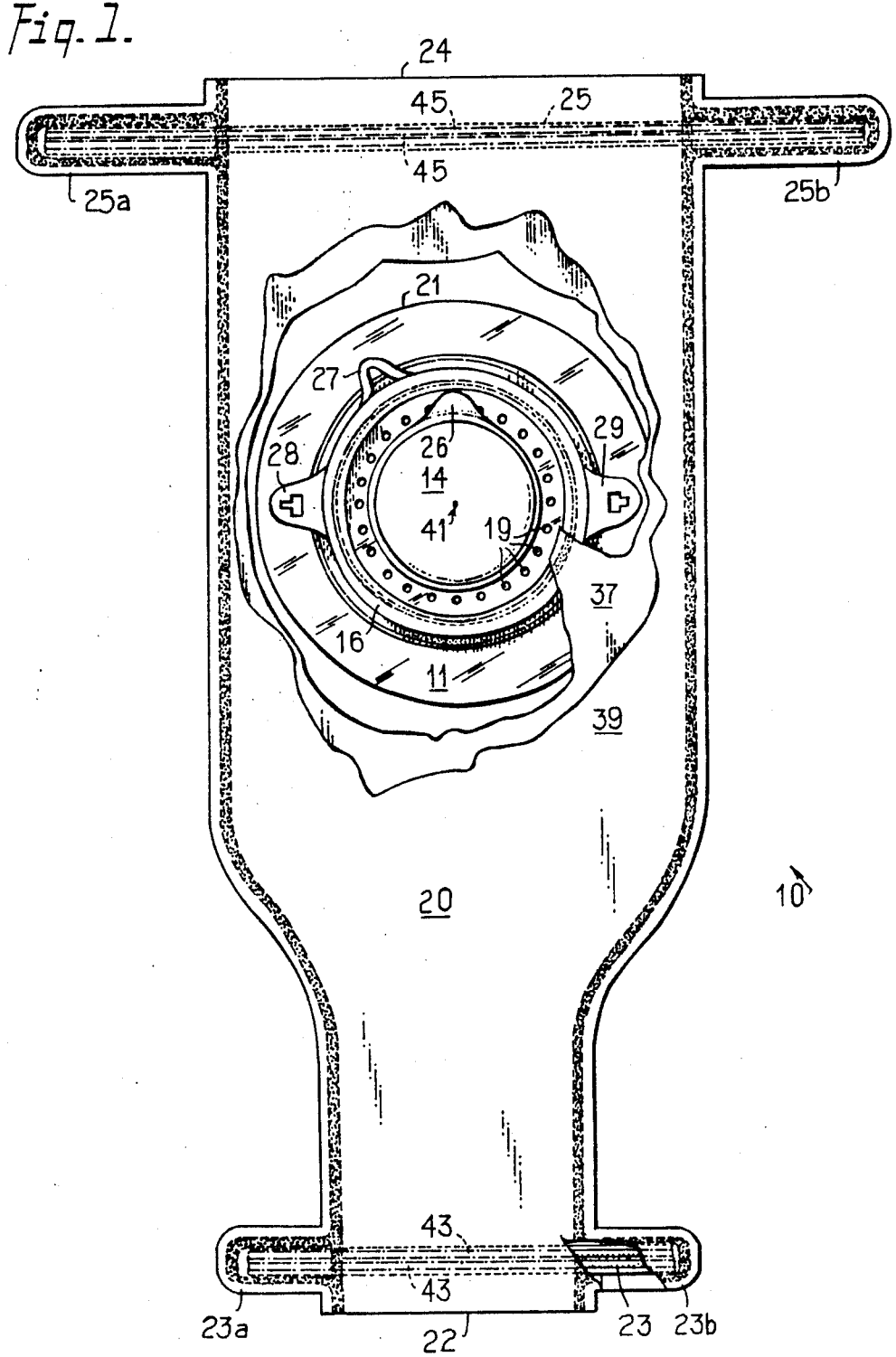
FIG. 1 is a plan view of the ostomy-plug pouch according to the present invention in which sections of both the front and back layers of the pouch have been cut away to show the support pad.

In FIGS. 1-4, the ostomy plug-pouch is indicated generally by the reference numeral 10. The plug-pouch 10 comprises a plug 14, a pouch 20, and a pad 11. The pad 11, on which the plug and pouch are detachably mountable, has a highly flexible panel 47 capable of conforming readily to body contours and movements. The material of which the panel 47 is fabricated is preferably sufficiently microporous that it is gas-penetrable but water resistant. The panel 47 is also preferably surface-coated with a porous thermoplastic film 49 which is heat sealable. Various materials having the properties described for the panel 47 and the film 49 are known and described in U.S. Pat. No. 4,610,676.

The pad 11 includes two generally concentric coupling rings 12 and 13 which may be secured to the film 49 by heat sealing or by any other suitable means. A grooved ring 16 similarly secured to an outside surface of the pouch 20 is sized to receive the coupling ring 13 (FIG. 4). In the coupling ring 12, on the other hand, a shoulder 51 provides means for latching the ring 12 to an inner rim 44 of the plug 14 to form a leak tight closure when the plug is mounted on the pad 11. A release handle 26 on the cap 14 is provided to facilitate dislodging the rim 44 from the shoulder 51 when removal of the plug 14 is desired. Connected to a cap 54 of the plug 14 by a flexible film 55 is a seal 15 which is inserted into the stoma. The seal 15 is made of material that swells when it comes into contact with the natural moisture in the intestine, thereby forming a secondary seal of the stoma.

The back side of the pad 11 is equipped with an adhesive surface 17 that may be either joined directly to the patient's body or to the outer surface of a thin protective underpad 18. When the pad 11 is to be fastened to the outer surface of the underpad 18, the inner surface of the underpad 18 is preferably an adhesive surface suitable for attaching to the body. The use of the underpad 18 stops irritation to the skin if leakage of the plug should occur.

The pad 11 also includes a plurality of small relief ports 19 disposed generally along the periphery of a circle concentric with and situated inwardly of the coupling ring 13. Each port 19 measures, by way of example, 1/16th inch in diameter. It is well known that when leakage of a stoma plug occurs, the site of the first failure is through the adhesive surface. The relief ports 19 direct such leakage to occur between the two rings 12 and 13 so that the leakage will be contained in the pouch 20. Without the relief ports 19, there would be a tendency for fluid to escape to the outer edge 21 of the pad 11, thus causing embarrassment and skin irritation to the patient.

The pouch 20 is constructed basically of thin waterproof plastic film layers 37 and 39 that are permanently fixed together along their side edges. The bottom of the pouch has a drain which is sealed by folding the bottom edge 22 of the pouch over a folding bar 23 held in place by tabs 23a and 23b and by then wrapping the lower portion of the pouch around the bar before bending the ends thereof back on itself. The folding bar 23 contains fine metal wires 43 that stiffen the bar; and when the tabs 23a and 23b are bent over, the wires 43 add sufficient stiffness to retain and seal the drain when the pouch is so wrapped. The length of the pouch 20 is sufficient that a patient sitting on a toilet is able to drain the pouch into the toilet without removing any more clothing than a person not encumbered with an ostomy pouch.

The pouch 20 also contains an openable and resealable top 24. In the preferred embodiment, the top 24 is sealed in similar fashion as is the drain, with the use of a folding bar 25 inserted into a pair of tabs 25a and 25b and having fine metal wires 45 embedded in the bar to stiffen it. When the top 24 is sealed, it is folded several times around the folding bar 25 and then secured in position by bending over the ends of the bar within the tabs 25a and 25b. The opening in the top is large enough for the patient to place his hand in the pouch and remove the plug 14 or to install a new plug 14 into the stoma.

The ostomy pouch-plug also facilitates the explusion of gas that may be formed in the intestine without embarrassment on the part of the patient. A small hole 41 in the plug 14 allows such gas to escape the plug. In addition, the pouch 20 has a vent 42 which communicates with openings in a filter 46 containing activated charcoal or the like to absorb the odor-producing fraction of the gas.

Figure 5:
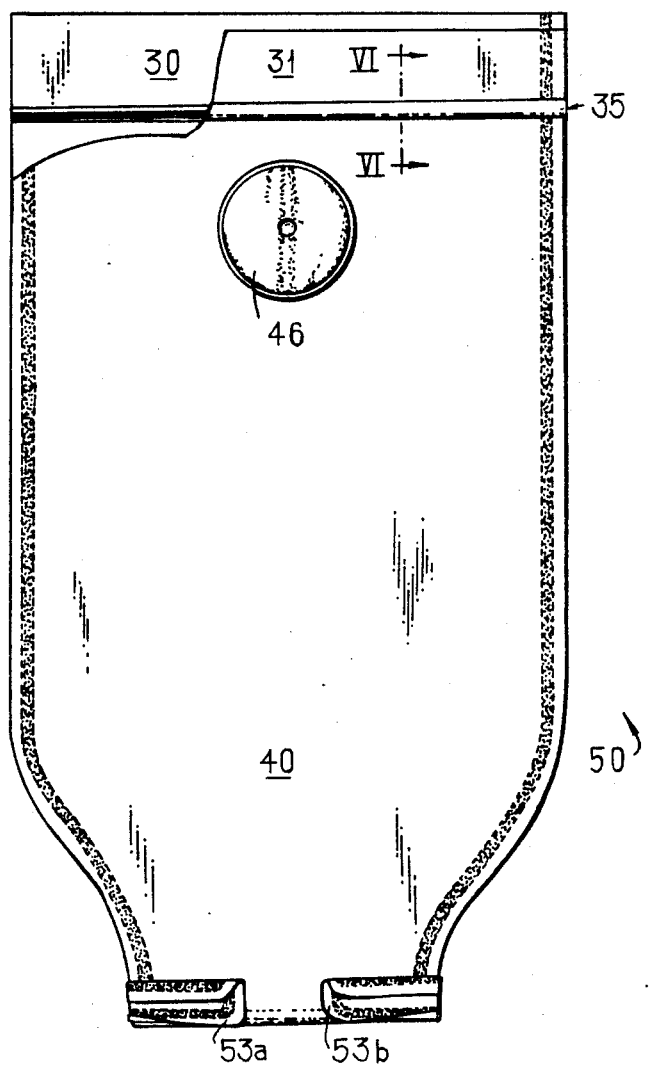
FIG. 5 is an alternate embodiment of the ostomy-plug pouch with a different design for the top closure.
Figure 6:
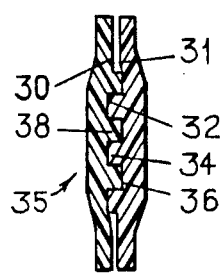
FIG. 6 is a cross-section VI—VI through the top closure in FIG. 5.

In FIGS. 5 and 6, an alternate embodiment of the ostomy plug-pouch indicated generally by the reference numeral 50 is illustrated. A pouch 40 in the plug-pouch 50 is similar to the pouch 10 but differs in the construction of means for closing the top of the pouch. As shown in FIG. 5, the pouch 10, like the pouch 40, not only includes a filter 46 but also tabs 53a, 53b similar in construction and use to the tabs 23a, 23 b. A closure 35, which distinguishes the pouch 40, includes alternating rows of raised ridges 38 and grooves 32, the ridges 38 protruding outwardly from the inner film layer 30 of the pouch 40. The rows of ridges 38 and of grooves 32 are so arranged that they can be interlocked with grooves 36 and with ridges 34, respectively, situated on the outer film layer 31. The contiguous surfaces of the layers 30 and 31 when lightly pressed together at the closure 35 form a liquid and gas tight seal.

While only two embodiments of the present invention has been disclosed herein for purposes of illustration, it is obvious that many variations and modifications could be made thereto. It is intended to cover all of these variations and modifications which fall within the scope of the present invention, as defined by the following claims:

It is claimed:

1. An ostomy pouch and stoma plug apparatus comprising:
   (a) a support pad having a hole of sufficient size to allow the stoma to be passed therethrough, coupling rings protruding from a first side of the support pad, the smaller of the two rings being encircled by the larger, the support pad having an adhesive surface disposed on a second side thereof;
   (b) a stoma plug having means for sealing the stoma and having a cap with a rim means, the smaller ring having a shoulder engageable with said rim means so that the cap can be coupled to the smaller ring to form a liquid and gas tight seal;
   (c) a pouch detachably mountable on the support pad, the pouch having a grooved ring for receiving a protruding portion of the larger ring on the support pad; and
   (d) a plurality of relief ports disposed between the two coupling rings, each port being spaced apart from said hole in the support pad, any fluid communication between each port and the hole being along a pathway which impedes direct fluid flow, so that any leakage from the stoma plug that penetrates beneath the adhesive surface between the stoma plug and the relief ports can exit through the ports and can be contained within the pouch.

2. The apparatus according to claim 1 which further comprises a thin underpad that is fastened to the support pad, the underpad including a cutout which allows the underpad to be fitted over the stoma prior to attachment of the adhesive surface of the support pad to the underpad, the underpad being constructed of a material impermeable to liquids in order to resist any leakage of the stoma plug beneath the apparatus.

3. An apparatus according to claim 1 that further comprises a vent for releasing natural gas discharges from the pouch and means for eliminating any odor from said discharges including a charcoal filter.

4. An ostomy pouch adapted to be worn by a patient with a stoma, the pouch comprising a support pad having a hole of sufficient size to allow the stoma to be passed therethrough, the support pad having an adhesive surface attachable to the patient, the pouch being affixed to the periphery of the pad surrounding the stoma, wherein the improvement comprises a plurality of relief ports, disposed between the stoma and the points of attachment of the pouch to the support pad, each port being spaced apart from said hole in the support pad, any fluid communication between each port and the hole being along a pathway which impedes fluid flow, so that any leakage between the stoma and the relief ports that penetrates beneath the adhesive surface of the support pad can exit through the ports and be contained within the pouch; a stoma plug having means for sealing the stoma to the support pad at locations situated between said hole and the relief ports.

5. An ostomy pouch and stoma plug apparatus which comprises:

(a) a support pad that is adhesively attachable to the body, said support pad having inner and outer rings, for detachably mounting an ostomy pouch to the body, and has a aperature of sufficient size to allow the stoma to be fitted therein;
(b) a removable plug means for sealing the stoma to said inner ring to prevent discharge directly from the stoma; and
(c) the support pad having a plurality of relief ports disposed between said hole and the points of attachment of the pouch to the support pad, each port being spaced apart from said hole in the support pad, any fluid communication between each port and the hole being along a pathway which impedes direct fluid flow, so that any leaking occurring in the plug of the stoma flows into the ostomy pouch.

6. An ostomy pouch and stoma plug apparatus according to claim 5 that further comprises an openable and resealable top which can be opened to allow one to remove said plug of the stoma.

* * * * *